United States Patent
Harper (12)

(10) Patent No.: US 6,357,171 B1
(45) Date of Patent: Mar. 19, 2002

(54) METHOD FOR AERIAL DISTRIBUTION OF POLLINATING AGENTS

(76) Inventor: William A. Harper, 16541 Redmond Way PMB #140, Redmond, WA (US) 98052-4492

( * ) Notice: Subject to any disclaimer, the term of this patent is extended or adjusted under 35 U.S.C. 154(b) by 32 days.

(21) Appl. No.: 09/664,757

(22) Filed: Sep. 19, 2000

(51) Int. Cl.$^7$ ............................... A01H 1/02; A01G 7/00
(52) U.S. Cl. ............................................ 47/1.41; 449/1
(58) Field of Search .......................... 449/1, 2; 47/1.41; 119/416, 427; 89/1.1

(56) References Cited

U.S. PATENT DOCUMENTS

| | | | |
|---|---|---|---|
| 4,075,783 A | * | 2/1978 | Burden et al. ................ 47/1.41 |
| 4,260,108 A | | 4/1981 | Maedgen |
| 4,644,683 A | * | 2/1987 | Jones .......................... 47/1.41 |
| 4,859,377 A | * | 8/1989 | Shasha et al. ................ 264/4.1 |
| 4,966,329 A | | 10/1990 | Show |
| 5,358,863 A | * | 10/1994 | Quimby, Jr. et al. ........ 435/178 |
| 5,484,504 A | | 1/1996 | Tedders |
| 5,785,245 A | * | 7/1998 | Tedders, Jr. et al. ............ 239/9 |
| 5,965,149 A | * | 10/1999 | Silver ......................... 424/405 |
| 5,996,276 A | | 12/1999 | Carter |
| 6,010,390 A | | 1/2000 | Harper |

OTHER PUBLICATIONS

North Dakota State University, NDSU Extension Service, North Dakota Agricultural Experiment Station, "Sunflower Production, Hybrid Selection and Production Practices", Publication EB–25, Jul. 1995. (http://www.ext.nodak.edu/extpubs/plantsci/rowcrops/eb25w–5d.htm).

McGregor, S. E., "Insect Pollination of Cultivated Crop Plants", USDA–ARS Agricultural Handbook, No. 496, pp. 345–351, 1976. (http://gears.tucson.ars.ag.gov/book/chap9/sun.html).

\* cited by examiner

*Primary Examiner*—Peter M. Poon
*Assistant Examiner*—Jeffrey L. Gellner

(57) ABSTRACT

Disclosure of a method for aerial distribution of pollinating agents into a field by either propelling the agent through the air from the field periphery or dropping the agent into the field from above. Aerial distribution of pollinating agents is a particularly effective, efficient, and economic means for achieving uniform saturation pollination of large fields of row crops.

28 Claims, No Drawings

METHOD FOR AERIAL DISTRIBUTION OF POLLINATING AGENTS

BACKGROUND OF THE INVENTION

1. Field of the Invention

This invention discloses a novel method for aerial distribution of pollinating agents into a field by either propelling the agent through the air from the field periphery or dropping the agent into the field from above. Aerial distribution of pollinating agents is a particularly effective, efficient, and economic means of achieving uniform pollination of large fields of row crops.

2. Background Art

Plant pollination by the honeybee (*Apis mellifera*) is by far the most common means of commercial crop pollination in the world. This pollination method depends on a single key element in honeybee natural history, the insect's social nature that is physically expressed as the beehive. Because the beehive is the essential center of any honeybee's existence the entire colony of 20,000 to 40,000 bees can be controlled by manipulation of the hive, and the business of a migratory beekeeper is largely based on moving hives about the country to pollinate crops for profit. A single hive typically weights 80 to 120 pounds, occupies about 9 cubic feet, and is filled with a delicate matrix of cells containing food, material, and developing bees essential to the operation and survival of the colony. Hive-based commercial migratory pollination is a place-and-retrieve operation where the honeybee hive is brought to the field for the duration of the bloom, subsequently retrieved from the field, loaded on flatbed trucks, transported to the next bloom locale, and deployed once again to service a new orchard or field. The logistics of the field deployment requires heavy equipment in the form of front loaders to load, unload, and position the hives at convenient access points near the target cultivar. For large field crops like sunflowers, canola, cotton, peanuts, mustard and similar cultivars the hives are distributed in clusters at the edges of the fields. Such large cultivar monocultures range in size from relatively small fields of 40 acres to mile-long sections containing hundreds and even thousands of acres. And in most nations, including the United States and Canada, the trend continues towards larger farms with even larger row crop fields that maximize the inherent efficiencies of mechanization and the growing practice of precision agriculture. This trend has continued despite clear evidence over several decades that shows honeybee hives placed at the periphery of these large-scale monoculture do not adequately pollination much of the field's interior.

Sunflowers are an example where a less than optimal crop is produced by inadequate pollination agent distribution. Sunflowers originated in the High Plains of North America where native and early cultivar varieties of the sunflower were self-incompatible and required indigenous insect pollination for a viable seed crop. As mechanization made larger fields possible the numbers and distribution of these native pollinating agents became too low to ensure an adequate seed set and crop yields declined. Sunflower hybrids were selectively breed to possess high levels of self-compatibility to overcome this pollination problem by simply not requiring a pollinating agent to produce a seed. And though self-compatible sunflower hybrids usually outproduce self-incompatible varieties in mass plantings, it is also known that many of these modem hybrids will actually produce even better when adequately pollinated by insects. Literature from several recent investigations indicates that in most modem sunflower hybrids, seed set, seed oil percentage, seed yields, and oil yields increased when pollinators (primarily bees) were present Yields increased as much as 48.8 percent and oil percentages increased 6.4 percentage in hybrid crops fully exposed to bee pollination activities (North Dakota State University, 1995). The problem is that the physical dimensions of large fields prevent pollinator penetration much beyond a relatively narrow band along the edges where the honeybee hives are placed. The problem of pollinator placement for sunflowers has been well understood for several decades. In the 1970's McGregor's classic work on pollination summarized the many findings to that time by simply stating "If there is a shortage of honey bees in the sunflower fields, a small seed crop is harvested" (McGregor, pp. 345–351, 1976). McGregor discussed many studies that indicated the benefits of pollination beyond roughly 300 feet from the honeybee hive became difficult to detect if found at all. To prevent the sharp decline in crop yield from inadequate pollination the practice of convergence or saturation pollination was recommended where the hives are to be distributed in a pattern that uniformly disperses the bees throughout the entire field. In the United States the specific distribution pattern advocated in 1962 was for distributing the honeybees every tenth of a mile (528 feet) in each direction in the field so the flight radius would only be some 264 feet. In the hybrid field plantings of today with higher plant densities per acre, larger seed heads, and more uniformity of bloom timing this 40-year old recommendation for a radius flight distance is probably much too high to achieve an actual condition of saturation pollination. In a typical mile-long quarter section (5280×1320 feet, 160 acres) sunflower field with hives uniformly spaced around the edge, over 75 percent of the plants can receive no effective honeybee pollination. Larger fields have correspondingly higher percentages of inadequate pollination; even a relatively small square field of 40 acres can have 50 percent of its area inadequately pollinated. The usual reasons given by the migratory beekeepers why hives can not be uniformly distributed within a field are the significantly greater, if not impossible, time and logistics requirements associated with the placement, maintenance, and retrieval of hives located at hundreds of points in a field. Clustering hives located at a relative few points around the edges is the only practical method of dispersal. Reasons given by the growers for no interior dispersal are equally clear, they do not want hive access alleys cut into their crops. Such inroads exposes the plants to wind damage, aids in weed establishment, entails crop land loss, promotes soil compaction, provides pest access, contributes to soil erosion, and the widely dispersed hives constrain spraying schedules while in general creating both work and inconvenience. The grower simply does not need more things to do, monitor, and worry about. Less than optimal sunflower hybrid crop yields without the aid of a pollination agent are acceptable as long as the costs, problems, and inconveniences of uniformly distributing honeybee hives are greater than the potential benefits.

Similar insufficient pollination conditions exist for other large field crops such as canola, cotton, mustard, peanuts, safflower, soybeans, and tomatoes. In each case these crops are grown in very large monoculture fields that would substantially benefit by a uniform pattern of saturation pollination it could be made practical and economical. And in each case the hive method by virtue of its weight, size, damage sensitivity, heavy equipment logistics, and retrieval requirements has proven inadequate in providing a pollinating service beyond a narrow band some 250 feet from the field's edge that leaves much of the crop area simply underdeveloped.

No known technology exists for the aerial distribution of pollinating agents into a field by launching them from the field's periphery or dropping them from above through the air. Obviously the honeybee hive by weight, size, and delicate cell structure is not a candidate for such deployment; the image of a beehive being catapulted through the air may have a precedent in ancient marine warfare but not crop pollination. Dropping a hive even a few feet is sufficient to cause significant interior damage and produce long-term injury to the honeybee colony. No one has achieved aerial distribution of honeybee nests as a viable means of distributing pollinating agents in field crops.

While the concept of successfully distributing pollinating agents by aerial means is novel and new, the literature has examples of methods for the distribution of biological control agents (parasite/predator insects) by various means including aerial. Maedgen (U.S. Pat. No. 4,260,108) first taught the simple "airborne release and broadcast of loose parasite/predator insect eggs for biological control of insect pests." Show U.S. Pat. No. 4,966,329) advanced the art by distributing predatory mites in a carrier material that required the adequate mixing of the materials and subsequent blowing the particulate/mite mixture on to plants. Tedders (U.S. Pat. No. 5,484,504) introduced another form of carrier for predaceous insects in the form of a string with attached eggs that could be cut "in predetermined lengths to be manually placed on individual plants." Most recently, Carter (U.S. Pat. No. 5,996,276) teaches the use of a biodegradable delivery device (a container) for dispersing biocontrol agents into a field by aerial means. The throwing tool is a mechanical device similar to those used in casting clay pigeons for skeet target practice; the delivery device, a hollow clay pigeon. The biological control agents are described as means to biologically control insect pests as an alternative to chemical insecticides, a desirable benefit in the health-conscious marketplace. The preferred embodiment describes an aerodynamic, biodegradable saucer shaped delivery device containing parasitic wasps. A variety of suitable biological control agents are listed for such deployment, "*Lygus hesperus*, parasitic wasps such as *Aphaelinus nr. paramali*, lacewing eggs, parasitic or predaceous mites and spiders, nematodes, and viral or bacterial agents." None of the above teachings nor any of their incorporated references suggest, whether taken singly or in combination, the deployment of anything other than biological control agents for the control of insect pests in crops.

A second background area, apart from the aerial distribution of rapacious insects, is that of pollinating methods. Harper (U.S. Pat. No. 6,010,390) teaches a novel alternative pollination method to the honeybee hive system and describes a non-aerial delivery system used for pollination distribution in orchards. Distribution is "by means of an appropriate container conveying said pollinating insects." The containers are termed field boards and are described as measuring 20×25×4 cm, each containing 130 cocoons of solitary bees, and are hand-carried for dispersal into an orchard. Harper neither addresses nor suggests how the problems of large-scale field pollination should or could be handled; the sole distribution method described is for an orchard where "the grower can walk the boards to optimum locations regardless of muddy conditions, narrow lanes or mass plantings." Harper also recites a number of United States patents that describe the management of various solitary bee species, but none describe nor suggest any aerial distribution means.

The present invention is superior to and an original departure from the current state of the art. First, the invention uniquely provides a viable means for aerial distribution of pollinating agents uniformly throughout large, densely packed fields of row crops not possible to accomplish with the present honeybee hive or solitary field board systems. Second, the invention describes a delivery device means for transporting the pollination agent which is able to withstand the destructive forces associated with being aerially propelled or dropped over significant distances into a field. A critical element making this pollination deployment invention possible was the discovery by experimentation that pollinating insects such as solitary bees are capable of withstanding the significant inertial forces associated with launch acceleration and landing impacts. Third, the invention solves a recognized pollination problem of at least forty years duration that remained unresolved before this teaching. Finally, the invention provides a means for achieving unprecedented levels of increased production on more than 35 million acres of United States and Canadian croplands presently significantly under served by the current practices of the pollination art.

SUMMARY OF THE INVENTION

It has been discovered that pollinating agents can be effectively and uniformly distributed by airborne techniques utilizing the present method. By this method the inaccessible interior of large row crop fields and other inaccessible plant areas where inadequate pollination exists can be provided with sufficient pollinators. The ability to distribute pollination agents uniformly throughout such circumstances provides for enhanced crop production, more options of cultivar and crop choice, and a superior return on the investment made to produce a crop.

A primary object of the present invention is to provide a method of deploying pollination agents by aerial means sufficient to provide plant pollination uniformly throughout a field.

Another object of the present invention is to provide a means for distributing pollination agents by propelling the agents from a field periphery or dropping the agents from above into a field by use of delivery devices that bear the agents so they settle in a predetermined pattern.

Another object of the present invention is to provide an engineered delivery device with shapes, sizes, and other characteristic which govern such attributes as launchability, flight control, landing attitude, agent protection, agent release, nesting support, device longevity, plural agent support, multi-device separation, and biological control features.

Another object of the present invention is to provide ecologically sound pest control by combining both pollination and biological control agents in one deployable delivery device.

Yet another object of the present invention is to significantly enhance crop production and crop variety choice through saturation pollination technology applied to such diverse cultivars as beans, canola, cotton, mustard, peanuts, safflower, soybeans, sunflowers and tomatoes.

A final objective of the present invention is to provide a technology whereby restoration of native pollinators in remote wildernesses, fragmented habitats, and similarly impacted natural areas is feasible so the natural food chain damaged due to extinct or diminished numbers of indigenous pollinators becomes once again a viable infrastructure capable of rebuilding and sustaining a robust ecosystem.

DETAILED DESCRIPTION OF THE INVENTION

The term "living organisms" as used herein refers to any animal, typically of Arthropods, incorporating the class Insecta, and including but not limited to the orders of Anoplura, Coleoptera, Dermaptera, Diptera, Embioptera, Hemiptera, Hymenoptera, Lepidoptera, Neuroptera, Orthoptera and Thysanoptera; all of which include species and subspecies that pollinate plants by their activities. Specifically included in this term are new species and subspecies identifiable by accepted taxonomic classifications as may be discovered or created that prove to be effective pollinators.

The term "pollinating agent" as used herein refers to any living organism that by its actions can pollinate at least one plant such as an entomophilous plant. Representative examples of such agents are the Insecta species collectively described as solitary bees; two specific examples of solitary bees are *Megachile pugnata* and *Osmia lignaria*.

The term "field" as used herein refers to any designated vegetated area containing at least one plant target of a pollination agent. Typically the term is used herein to define an area of cleared enclosed land used for at least one of any type of cultivar capable of benefiting from pollination; also, as used herein, this term includes uncultivated areas of flora in which plant pollination is enhanced by introduction of a pollination agent. The term specifically includes the situation where the delivery device bearing the pollination agents lodgings in plant foliage above the ground as being fully within the concept of landing on the ground in the field.

The term "delivery device" as used herein refers to any container capable of holding, protecting, and releasing pollinating agents among plant capable of being pollinated. Typically, the term used herein describes a container having a shape, size, and other characteristic that governs such attributes as launchability, flight control, landing attitude, agent protection, agent release, nesting support, device longevity, plural agent support, multi-device separation, and biological control features. The term encompasses a delivery device engineered to be capable of withstanding the mechanical stresses on the device during launch, flight, and landing while providing protection to the living organisms within it. Equally encompassed is a relatively simple container having only the fundamental capabilities to hold, protect, and dispense without any attention to aerodynamic design features or stress conditions beyond normal handling.

The present invention can best be understood by several examples that illustrate how a delivery device bearing a pollinating agent is dispersed through the air. Each is a preferred embodiment of a typical element of the method for aerial distribution of pollinating agents. Each of these non-limiting examples illustrates a possible embodiment and various refinements.

EXAMPLE 1

Delivery Device Description

The delivery device in its simplest configuration is a container that holds, protects and disperses the pollinating agents. Propelling or dropping the delivery device through the air creates an aerial pollination distribution method of significant efficiency, and most often requires of the delivery device to have specific design features that facilitate this form of distribution. The following description of a delivery device is an example of one possible configuration among many; it is a design of a general-purpose delivery device useful in either propelled or dropped applications. Its deployment will be used to illustrate the pollination method applied to a mid-sized sunflower field in the following examples.

The side profile of the delivery device is reminiscent of an old Civil War rifled artillery shell. It is a cylinder approximately 5 inches long and 3.5 inches in diameter, the front-end is domed and the backend is flat. The actual materials used in the delivery device are all biodegradable; for example, the outer 3.5-inch casing is a cylinder of laminated papers held together by a soluble paste which in a predetermined period of a few weeks will dissolve and contribute to the break down of the delivery device. This exterior casing cylinder with a 0.125-inch thick wall holds together on its immediate inner surface the first of three concentric layers of 100 nesting tubes, each one of the three layer contains 41, 33, 26 individual nesting tubes as counted toward the center respectfully. Each of the nesting tubes has a 0.3125-inch interior diameter and only a few windings of paper to form its thin wall. Holding the nesting tubes in place against the outer casing is an inner cylinder with an interior diameter of 1.625 inches and a mid-sized wall thickness, the cavity formed within this cylinder is the pollinator chamber with a useful volume of about 9 cubic inches. The nesting tubes are 4.25 inches in length, both the exterior casing and the pollinator casing are 4.5 inches long. The domed front-end nose piece is about 1.3 inches thick at its greatest depth, is made of solid material such as compressed paper pulp or soil with a binder, and is noticeably heavier than the rest of the delivery device. Three purposes are served by the nosepiece; it is weighted forward to provide ballistic control in flight, its solid construction provides damage control on landing, and it holds together the various interior and casing cylinders that are securely embed in it from the rear forming one unit. All the cylinders are blocked at the front-end by virtue of being embedded in the nosepiece, all the backends are open. Into the pollination chamber about 200 diapausing mason bees (*Osmia lignaria*) in cocoon weighing about 1.5 ounces are placed; they are the pollinating agent. (Selection of the mason bee as the pollinator is done because their cocoons are relatively large for North American solitaries and usefully demonstrate how the volume and weight issues associated with aerial pollination deployment are not constraining design factors. There are a number of better-adapted sunflower pollinators among the thousands of solitary bee species in North America than masons; one example is the sunflower bee, *Megachile pugnata*. In this example, 200 masons are deemed sufficient for a half acre of hybrid sunflowers.) Only about 60 percent of the of the chamber's volume is filled by the cocoons so light padding in the form of crumpled paper or cotton is added first to prevent unnecessary movement and cushion the impact. A seal is placed over the pollinator chamber to contain the cocoons, the bees upon breaking diapause will chew through the seal to emerge from the delivery device. The nest tubes remain open to provide nest sites for the emerged solitaries so they will be encouraging to remain in the target area during their pollination activities. The delivery device weights about 6 ounces with the nosepiece being the single heaviest component.

There are many potential pollinating agents that can be transported by the delivery device to a target area and plant. Each might well require modifications to the delivery device in order to be successfully deployed following a landing. Some pollinators, for example, might not be as aggressive as many solitaries in chewing their way to release and need a less resistant path of breaking the seal themselves for a successfully deployment. To facilitate this (and by way of an example of the design adaptability of the delivery device) a rigid rod can be placed so as to protrude outward from the center of the nosepiece by an one inch and continue through the center of the delivery device so the opposite flattened end rests on the underside of the seal. A small adhesive patch keeps the rod in position during aerial deployment but upon landing the impact pushes the rod to the rear, breaking open the seal, and permitting unfettered pollinator release through the ruptured seal barrier.

Nesting tubes are not a critical component to the delivery device in all cases, they assists in keeping some solitary pollinator in the target area by providing a ready and convenient nesting site while encouraging a rapid start to pollination activities which provide the supplies for nest building. Other solitary and other non-social pollinators like some flies will seek out nearby natural habitats. The use of the nesting tubes in this example of a delivery device is that of a feature and not a critical element of the aerial pollination method specification. Another feature within this context would be the old-fashion artillery shell shape of the delivery device. This shape is a proven, simple design that has an excellent capacity for stable flight and target acquisition. Examples of enhancement features to improve the aerodynamics characteristics and targeting ability are adding a rifling sabot for rotation when propelled or stabilizing fins when dropped. Another feature that could be employed would be means to control the final resting attitude of the delivery device upon landing. By engineering the exterior shape to facilitate how the delivery device comes to rest, features like the open exposure and subsequent access to the nesting tube entrances can be assured. Use of the weighted nosepiece virtually assures the delivery device lands nose down and topple over on to its side as designed. The delivery device is essentially nothing more than a container conveying the pollinators through the air to a selected landing site. A key requirement is that it keeps the pollination agents together and protected during the aerial trip. The shape and internal structures could be any of a number of interacting geometric forms including by way of example a circular ring, cone, cube, cylinder, disc, ellipsoid, frustum, hemisphere, paraboloid, parallelepiped, prism, pyramid, rectangular prism, sphere, spheroid and combinations thereof that provide sufficient structural strength and cohesion to survive the deployment.

Another possible feature to incorporate into a delivery device would be to utilize a design where many smaller sub-unit delivery devices are capable of being dispersed after being launch as a single delivery device. One launched delivery device could disperse many smaller delivery device over a target area leading to creation of a highly dispersed pattern of pollinators which may not have flight capabilities. In these circumstances it is very desirable to reduce the crawling distance to a minimum so as to assist pollination activity. Many small, closely dispersed units from one released unit would be a more efficient technique than attempting to control each small unit uniquely. In this instance the effective deployment could be further helped by the delivery device lodging in the plant foliage above the surface of the ground. This condition would be considered a successful landing. Pollinators are food for many animals and field deployment will often serve up a treat for a number of natural predators as diverse as skunks, raccoons, birds, shrews and the like. A chemical repellant can be incorporated into or onto the delivery device to forestall such depletion. Simply dipping or spraying one or more appropriate repellant compound is sufficient. Another form of attack upon the pollinators can come in the form of fungi usually from the soil. Again, treatment of the delivery device by spraying or dipping with the appropriate fungicide is the appropriate action. A final example of a feature that can prove use to the delivery device is to employ a rotational airfoil glider design in the style of Frisbee discs. Both greater distances and flight control are possible with this design. Also airfoils with relatively high ratios of surface to weight will quickly slow forward motion when dropped, hold on target, and produce softer landing. The number of features possible to incorporate with a delivery device is quite large and fully contemplated within the scope of such diverse areas as antipersonnel weaponry, recreational toys, bio-engineering and like subjects as may be usefully applied to aerial pollination.

EXAMPLE 2

Aircraft Dropping Delivery Devices

Using aircraft to distribute pollinating agents into a field is by far the most efficient and economical method of deployment. Commercial aerial spraying and dusting of field crops has been a standard agricultural practice for decades and nearly all large fields are physically laid out to accommodate this particular form of crop maintenance. The same aircraft and operational tactics employed in these activities are well suited to deploying delivery device bearing pollinating agents; dropped like small bombs from the aircraft at regular intervals on repeated spaced passes over the field, an effective pattern for saturation pollination can be established. By varying the rate of release of the delivery devices by electromechanical means controlled by a microprocessor inputting the aircraft speed and other variables a remarkable number of pollination patterns can be deployed with considerable accuracy. For example, a field of 160 acres measuring 5280×1320 feet employing a distribution pattern of two units per acre requires 320 delivery devices on 146 foot centers laid down in nine passes. The total payload loaded on the aircraft is less than 16 cubic feet and 120 pounds based on individual unit canisters of 3.5×5 inches, 6 ounces. A delivery device is released from the aircraft every second at 90 miles per hour, 40 drops per pass on a 5280-foot run, from alternative under-wing pods to maintain the aircraft's load balance. Using a standard shaped delivery device unit dropped from aircraft a wide range of patterns, pollinators, densities, and materials can be placed in fields quickly, accurately, and with economy.

EXAMPLE 3

Propelled Delivery Devices

A second method of deployment is to propel the delivery device from the field periphery. While less efficient than aircraft deployment it can prove useful for smaller operations that chose not to employ a pilot and plane. The same delivery device can be used but the technique for the aerial delivery to the field interior is ground based. One very low cost propelling means is essentially a large slingshot made of surgical rubber tubing and lumber. This device, common on beaches and college campuses, built large enough can cast a delivery device 200 yards or more with surprising accuracy. Truck mounted, it can be conveniently moved to predetermine positions on the field's periphery and throw delivery devices into proper locations to form a pattern sufficient to provide saturation pollination. A second propelling means employs an oxyacetylene or oxy-propane cannon or mortar capable of shooting the delivery device as a shell even further. Again, mounted on a track with tanks of gases to supply the charge a sabotted shell can hit a target location with good accuracy. A third propelling means is a modified use of dummy launchers used to train retrieving dogs. While primarily for short-range work these hand-held launchers can throw a modified delivery device over 300 feet into a field. The launchers use 0.22-caliber dummy loads for propellant, are inexpensive, and are very reliable. Skillful use of this technique can provide a sufficient deployment pattern for saturation pollination. The fourth means of aerial deployment from the ground is simply to throw the delivery device into the field. For limited penetration this method can work, but for longer distances delivery device airfoil designs would be necessary to provide the glide and control aerodynamics. However propelled from the ground at the edge of targeted cultivars, the aerial distribution of pollinating agents can be accomplished sufficient to pollinate those cultivars surrounding the landing site of the delivery device.

EXAMPLE 4

Plural Species in Delivery Devices

Combining more than one species or subspecies in a delivery device can address the multiple pollination requirements of a field with mixed plant types each with specific species preferences such as blooming times and other diverse characteristics. A variation of this feature is the use of the same species in varying levels of development. By mixing development stage it is possible to have pollinators emerging throughout an extended time frame so varying blooming of different plants and plant species can all be pollinated well beyond the life cycle of the first emerging pollinators.

EXAMPLE 5

Patterns of Delivery Devices

To provide the maximum pollination advantage to the aerial distribution of pollinating agents it is necessary to establish a regular pattern of release sites. Uniformity of coverage leading to saturation pollination is based on an established pattern. This is especially true of solitary bees. Solitaries have no colony structure to provide specialized member functions such as scouts to be sent out to find the best pollen and nectar sources for literally miles in any direction. Individual solitary females alone do all the functions: provision gathering, nest building, and egg laying. The individual bee's energy schedule can simply not afford to look beyond a limited range of a few hundred feet for provisions and consequently strenuously works the bloom it does find within its range. This trait is very useful for keeping the solitary near its original nesting site, very valuable for thorough pollination, and underscores why a uniform pattern is necessary to assure saturation pollination. Poorly deployed delivery devices can leave holes in the pollination service that will not likely be covered by solitary drift from other nearby areas.

EXAMPLE 6

Pest Control in Delivery Devices

Incorporating one or more pest control materials into the delivery device provides a means of protecting the pollinating agents from numerous threats when repallants prove ineffectual, uneconomical, or unavailable. Lethal and sublethal control materials can be incorporated with or on to the delivery device. Examples would be to control rodents by mixing warfin into the delivery device's nosepiece as a rodenticide; a molluscicide applied to the exterior of the delivery device to deter snails and slugs from damaging the material before its engineered date of degrade; and, the placement of *Stelis montana* bees in the delivery device as a larvacide on the next generation of solitaries and thus control the potential long-term ecological damage created by the massive introduction of non-native pollinating agents. There are many variations on the basic principle of needing control material to prevent damage, some of these material include acaricides, avicides, biological control agents, chemosterilants, conventional toxicants, fungicide, growth regulators, herbicides, hormones, insecticides, larvicides, microbial control agents, miticides, molluscicides, nematicides, ovicides, parasiticides, pathogens, pesticides, pheromones, predicides, pupicides, repellents, rodenticides, sporicides, sterilants, systemics, vermicides, viricides and mixtures thereof Throughout this application various publications are referenced. The disclosures of these publications in their entireties are hereby incorporated by reference into this application in order to more fully describe the state of the art to which the invention pertains.

The foregoing examples are illustrative of the present invention, and are not to the constructed as limiting thereof. It will appear to those ordinarily skilled in the art that various modifications may be made to the disclosed embodiments, and that such modifications are intended to be within the scope of the present invention. The invention is defined by the following claims, with equivalents of the claims to be included therein

What is claimed is:

1. A method for delivering living organisms used as a pollinating agent by aerial means into a field, said method comprising:
    a) placing said living organisms into a delivery device;
    b) dropping or propelling said delivery device through the air into said field;
    c) landing said delivery device containing said living organisms in said field;
    d) releasing said living organisms from said delivery device into said field to pollinate.

2. The method of claim 1, wherein said delivery device is biodegradable.

3. The method of claim 1, wherein said delivery device incorporates a nesting site used by said living organisms.

4. The method of claim 1, wherein said delivery device is dropped from an aircraft into said field.

5. The method of claim 1, wherein said delivery device is propelled from the ground into said field.

6. The method of claim 5, wherein said delivery device is propelled from a handheld firing mechanism.

7. The method of claim 5, wherein said delivery device is propelled from a firing mechanism mounted on a vehicle.

8. The method of claim 1, wherein said delivery device is of an aerodynamic shape capable of remaining on course to a selected target area.

9. The method of claim 1, wherein said delivery device is an engineered shape and structured capable of withstanding the mechanical stresses on said delivery device during launch, flight, and said landing.

10. The method of claim 1, wherein said delivery device is generally formed in the manner of at least one geometric shape selected from a group comprised of a circular ring, cone, cube, cylinder, disc, ellipsoid, frustum, hemisphere, paraboloid, parallelepiped, prism, pyramid, rectangular prism, sphere, spheroid and combinations thereof.

11. The method of claim 1, wherein said delivery device is of an engineered shape so as to rest in a desirable attitude after said landing.

12. The method of claim 1, wherein said delivery device constitutes a plurality of said delivery device as sub-units which deploy by separating one from another following a common launch or release so each said sub-unit has a said landing independent of other said sub-units.

13. The method of claim 1, wherein said delivery device lodging in plant foliage above the ground is equated with said landing on ground in said field.

14. The method of claim 1, wherein said delivery device incorporates a material to repel undesirable animals actions.

15. The method of claim 1, wherein said delivery device contains a fungicide to protect the said pollinating agents.

16. The method of claim 1, wherein said delivery device is an airfoil engineered to achieve improved flight distances or control when propelled or dropped into said field.

17. The method of claim 1, wherein said delivery device is propelled or dropped by mechanical, explosive, gas pressure, or electromechanical means.

18. The method of claim 1, wherein said living organisms are Arthropods.

19. The method of claim 1, wherein said living organisms are of the class Insecta.

20. The method of claim 1, wherein said living organisms are selected from a group comprising the Anoplura, Coleoptera, Dermaptera, Diptera, Embioptera, Hemiptera, Hymenoptera, Lepidoptera, Neuroptera, Orthoptera and Thysanoptera orders.

21. The method of claim 1, wherein said living organisms are solitary bees.

22. A method for delivering living organisms used as pollinating agents into a field by aerial means, said method comprising:

a) placing plural species or subspecies of living organisms into a delivery device;

b) dropping or propelling said delivery device through the air into said field;

c) landing said delivery device containing said living organisms in said field;

d) releasing said living organisms from said delivery device into said field to pollinate.

23. A method for delivery living organisms used as a pollination agent uniformly throughout a field of cultivators, said method comprising;

a) placing said living organisms into a delivery device;

b) dropping or propelling said delivery device through the air into said field in sufficient numbers and in a regular pattern so as to be capable of providing uniform pollination saturation of said cultivars;

c) landing said delivery device containing said living organisms in said field;

d) releasing said living organisms from said delivery device into said field to pollinate.

24. A method for delivering living organisms used as pollinating agents and a pest control material into a field, said method comprising:

a) placing said living organisms into a delivery device;

b) incorporating said control materials with a delivery device;

c) dropping or propelling said delivery device through the air into said field;

d) said delivery device comprising a structure capable of retaining and securing said living organisms until said delivery device lands in said field;

e) releasing said living organisms from said delivery device into said field to pollinate.

25. The method of claim 24 wherein the said control materials are at least one compound selected from the group comprising of acaricides, avicides, biological control agents, chemosterilants, conventional toxicants, fungicide, growth regulators, herbicides, hormones, insecticides, larvicides, microbial control agents, miticides, molluscicides, nematicides, ovicides, parasiticides, pathogens, pesticides, pheromones, predicides, pupicides, repellents, rodenticides, sporicides, sterilants, systemics, vermicides, viricides and mixtures thereof.

26. A method for deploying at least two species of living organism for enhancing plant pollination, the first used as a pollinating agent and the second used as a biological control agent, said method comprising:

a) a delivery device, b) placing at least one type of pollinating agent into said delivery device;

c) placing at least one type of biological control agent into said delivery device;

d) deploying said delivery device among entomophilous plants;

e) releasing said organisms to pollinate or control biologically.

27. The method of claim 26 wherein the pollinating agent is selected from a group comprised of solitary bee species.

28. The method of claim 26 wherein the biological control agent is selected from a group comprised of parasitic and predacious insects of the class Insecta.

* * * * *